| United States Patent [19] | [11] | 4,427,647 |
|---|---|---|
| Brockas et al. | [45] | Jan. 24, 1984 |

[54] METHOD AND REAGENT FOR MAKING A RADIOPHARMACEUTICAL COMPOSITION BASED ON PERTECHNETATE

[75] Inventors: Anthony Brockas; Roy Abrahams; James D. Kelly, all of Amersham, England

[73] Assignee: Amersham International Limited, England

[21] Appl. No.: 286,752

[22] Filed: Jul. 27, 1981

[30] Foreign Application Priority Data

Aug. 12, 1980 [GB] United Kingdom ............... 8026198
May 15, 1981 [GB] United Kingdom ............... 8114935

[51] Int. Cl.$^3$ ..................... A61K 43/00; A61K 49/00
[52] U.S. Cl. ........................................ 424/1.1; 424/9
[58] Field of Search ........................................ 424/119

[56] References Cited

U.S. PATENT DOCUMENTS 3,962,412 6/1976 Wolfangel ............................... 424/1
4,075,314 2/1978 Wolfangel et al. ..................... 424/1

OTHER PUBLICATIONS

Dumortier et al., Int. J. Appl. Rad. Isotopes, 25 (1974) 189–191.

*Primary Examiner*—Christine M. Nucker
*Attorney, Agent, or Firm*—Wenderoth, Lind & Ponack

[57] ABSTRACT

A method of making a radiopharmaceutical composition by mixing an aqueous solution of pertechnetate with a reducing agent comprising tin metal or stannous ion to reduce the pertechnetate and a complexing agent to form a complex with the reduced technetium, is characterized by incorporating nitrate and/or nitrite in an amount to diminish oxidation of $Sn^{2+}$ to $Sn^{4+}$, and hence to prevent re-oxidation of technetium to pertechnetate, during preparation and storage of the complex. Nitrate and nitrite are superior to organic antioxidants previously proposed.

A reagent for the purpose comprises the reducing agent, the complexing agent and the nitrate and/or nitrite usually in a sterile freeze-dried state.

9 Claims, No Drawings

METHOD AND REAGENT FOR MAKING A RADIOPHARMACEUTICAL COMPOSITION BASED ON PERTECHNETATE

The radioactive isotope technetium-99m is a gamma emitter with a half life of about 6 hours and is very widely used in medical diagnosis. Technetium-99m is generally obtained as a sterile solution of pertechnetate ion $TcO_4^-$ in isotonic saline from a commercially available technetium generator. It is usually necessary to reduce the technetium from the +7 valency to the +3, +4 or +5 valency, in order to form, with a suitable complexing agent, a complex which has a desired property, e.g. upon introduction into a patient, of becoming localised in a desired organ.

The most widely used reducing agent for this purpose is stannous ion $Sn^{2+}$. Diagnostic kits frequently contain, in a sterile freeze-dried state, a mixture of stannous salt with a complexing (or chelating) agent for technetium. The kit is activated by aseptic introduction of an aliquot of generator eluate containing pertechnetate in saline. The stannous salt reduces the technetium, the complexing agent forms a complex with the reduced technetium, and the resulting sterile liquid is ready for injection into a patient. Many hospitals make up a single large batch of injection solution in the morning, which they hold for use throughout the day.

The designers of these kits are faced with two conflicting requirements:

(i) The tin content of the solution for injection should be as low as possible. An excess of tin tends to hydrolyse with the formation of technetium-tin colloids which locate in the reticuloendothelial system (liver, spleen etc.), thus degrading the biodistribution pattern. Also, tin is mildly toxic.

(ii) The solution for injection should not contain any significant amount of pertechnetate. Pertechnetate tends to be cleared only slowly from the blood and also to locate in the gut and thyroid, thus again degrading the biodistribution pattern.

Increasingly it has been recognised that injection solutions containing technetium complexes in chelates formed by the reduction of pertechnetate are prone to regenerate pertechnetate on storage. The problem becomes acute for solutions containing high activities of Tc-99m in relation to the stannous ion content, and the present tendency to employ larger and larger amounts of Tc-99m in a preparation aggravates the problem. It is believed that the problem arises because of depletion of the stannous salt present.

We have found with a variety of such scanning agents that, while stannous ion remains present in solution, pertechnetate is not formed but, once stannous ion has been used up (for example by oxidation by air or by radiolytic oxidation) pertechnetate begins to form.

As will be apparent, there are a number of theoretically possible solutions to this problem:

(a) Eliminate oxygen e.g. by nitrogen purging the eluate and kit vials. This is to some extent effective but very inconvenient, particularly when using multidose vials. Technetium generator eluent is often saturated with air in order to maintain generator yields; it would be tiresome to have to displace dissolved oxygen in the eluate before use.

(b) Use more stannous salt. This is undesirable for the reasons given above.

(c) Protect the stannous salt by means of an antioxidant. This is the solution advocated in a number of patent specifications, for example, British Nos. 1,489,330; 1,530,106; 1,541,070 and European Nos. 0004684; 0006658; 0006659 and 0007676. However, it is undesirable to have antioxidants present for this reason; they may be toxic, or they may react with the complexing agent or with the technetium and so degrade the biodistribution pattern. For example, ascorbic acid, a known non-toxic antioxidant and one of the most favoured compounds for protecting stannous salts, forms, in the presence of iron, a technetium iron ascorbate, a known kidney scanning agent.

Another reducing agent for pertechnetate is tin metal, as described in our British patent specification Nos. 2,016,198 and 2,036,000. One of the features of using tin metal as a reducing agent is that there is very little free stannous ion in solution; while this has a number of advantages, it may be risky if the technetium complex is liable to oxidation.

While the formation of complexes using metallic tin is not seen as simply the formation of $Sn^{++}$ followed by reduction of $TcO_4^-$, as the tin metal seems to play a more fundamental role than this, it nevertheless appears that the presence of a low concentration of $Sn^{++}$ improves the stability of the complex after its formation.

While we do not wish to be bound by theory, it is possible that the formation of stannous ion from metallic tin is slow and that the equilibrium concentration of stannous ion is therefore dependent on the amount of oxygen present in the solution—the more oxygen, the less stannous ion. The rate of oxidation of technetium complexes, when stannous tin levels are very low, may be proportional to the amount of technetium present.

The present invention results from our observations that nitrate and nitrite protect stannous ion from oxidation. This is unexpected, because nitrate is not known as an antioxidant; indeed, nitrate is known under some conditions to have very powerful oxidising powers. An advantage of using nitrate rather than a conventional antioxidant such as ascorbic acid is that nitrate is known to be non-toxic and not to form complexes with technetium in any valency.

The invention accordingly provides in one aspect a method of making a radiopharmaceutical composition by mixing an aqueous solution of pertechnetate with a reducing agent comprising tin as metal or $Sn^{++}$ to reduce the pertechnetate and a complexing agent to form a complex with the reduced technetium, characterised by incorporating in the composition nitrate and/or nitrite in an amount to diminish oxidation of $Sn^{2+}$ to $Sn^{4+}$ during preparation and storage of the complex.

It is known from British Pat. No. 1,361,988 that nitrate or nitrite may usefully be added to the saline used as technetium generator eluent to prevent loss of yield apparently caused by reduction of pertechnetate within the generator. In this prior patent, nitrate is exercising a pro-oxidant function, preventing technetium from being reduced from the +7 to a lower valency. This makes it all the more surprising that, in the present invention, nitrate exercising an apparently anti-oxidant function, preventing technetium from being oxidised from a lower valency to the +7 valency.

The invention provides in another aspect a reagent which forms, on addition of an aqueous solution of pertechnetate, a radiopharmaceutical composition, which reagent comprises in a sterile state a stannous tin reducing agent for the pertechnetate, a complexing agent to form a complex with the reduced technetium, and nitrate and/or nitrite ion in an amount to diminish oxidation of $Sn^{2+}$ to $Sn^{4+}$ during preparation and storage of the reagent and of the complex. The invention also provides reagents in which the stannous tin is replaced by tin metal.

Our research work has indicated that unwanted oxidation of tin from the +2 to the +4 valency takes place at several different stages. An example is provided by an MDP composition for bone scintigraphy containing 0.34 mg $SnF_2$ per vial:

(i) Solutions of stannous ion and methylene diphosphonate (MDP) are dispensed into vials. By the use of nitrogen purging, oxidation can be reduced at this stage.

(ii) The mixed solution is freeze-dried. In the absence of nitrate or nitrite ion, there are losses during dispensing and freeze-drying totalling about 20% of the stannous ion initially present.

(iii) The freeze-dried product may be sterilised by gammaradiation and stored. The loss at this stage is small.

(iv) The product is reconstituted with 8 ml of technetium generator eluate. Under conventional conditions, i.e. no nitrate or nitrite but with oxygen dissolved in the eluate, about 45% of the stannous ion is oxidised at this stage, in addition to that (tiny) proportion used up in reducing the pertechnetate.

(v) The reconstituted solution is stored for possibly a few hours before use. The loss of stannous ion at this stage is typically at a rate of 0.2 to 0.4 $\mu g/mCi/hour$, and is believed due to a radiolytic effect.

Since some of the loss of stannous ion occurs before addition of the pertechnetate, it is preferred that the nitrate or nitrite be added to the kit with the stannous ion and the complexing agent for reduced technetium. Alternatively but less preferably, the nitrate or nitrite may be added to the preformed technetium generator eluate; or may be added separately to the vial at the time of reconstitution.

When tin metal is used as a reducing agent, losses of stannous ion before addition of the pertechnetate are non-existent. Subsequently, the presence of nitrate or nitrite ion inhibits oxidation of stannous ion in solution, and the resulting greater equilibrium concentration of stannous tin prevents formation of free pertechnetate ion even when large amounts of activity are present.

Nitrite ion is effective at lower concentrations than nitrate. In the kind of system where technetium generator eluate containing up to about 500 mCi of activity is added to a vial, the presence in that vial of from 0.01 mg to 5.0 mg preferably 0.05 mg to 0.5 or 1.0 mg, of nitrite, expressed as sodium nitrite, and/or from 0.1 mg to 50 mg, preferably 0.5 mg to 5.0 or 10 mg, of nitrate, expressed as sodium nitrate, is effective to prevent the re-appearance of pertechnetate during the usable life of the solution. When larger amounts of pertechnetate are used, proportionately larger amounts of nitrate and/or nitrite are required.

At concentrations below these ranges, nitrate or nitrite may not provide effective protection. At concentrations within these ranges ample protection if provided and at higher concentrations there may conceivably be unwanted side effects of nitrate or nitrite.

Stannous ion may be added in any convenient non-toxic form e.g. as halide or sulphate. Nitrate may be added in any non-toxic form e.g. as the sodium, potassium or ammonium salt. Stannous nitrate could be used to supply part of the nitrate if this salt were sufficiently stable, but it is not.

The invention is believed to be applicable to all technetium kits that use metallic tin or stannous salts as reducing agents, examples of which are:

methylene diphosphonate: bone
gluconate or glucoheptonate: kidney
iminodiacetic acid derivatives (HIDA): liver
diethylenetriamine pentaacetic acid: brain/kidney The following Examples illustrate the invention. In each, comparative data is also included. Examples 1 to 6 use nitrate while Example 7 uses nitrite. Examples 1 to 4 and 7 use stannous tin while Examples 5 and 6 use tin metal as the reducing agent.

EXAMPLE 1

Preparation of technetium (MDP) agent for bone scintigraphy

Bulk aqueous solutions of methylene diphosphonate (MDP), stannous fluoride ($SnF_2$) and sodium nitrate ($NaNO_3$) were prepared. Aliquots were dispensed under nitrogen into vials to provide the following amounts:

| Formulation Code | Reagent | Amount per vial. |
| --- | --- | --- |
| 1F | MDP | 5.0 mg |
| 2F | MDP | 10.0 mg |
| 2.5F | MDP | 15.0 mg |
| 1F | $SnF_2$ | 0.34 mg |
| 2F | $SnF_2$ | 0.68 mg |
| 2.5F | $SnF_2$ | 1.02 mg |
| N5 | $NaNO_3$ | 0.5 mg |
| 1N | $NaNO_3$ | 1.0 mg |
| 2N | $NaNO_3$ | 2.0 mg |
| 4N | $NaNO_3$ | 4.0 mg |

The vials were dispensed and freeze-dried, and the loss of stannous ion was determined with the following results:

| Formulation Code | % Loss of $Sn^{2+}$ on Freeze Drying |
| --- | --- |
| 1F | 20 |
| 1F.1N | 0 |
| 1F.2N | 5 |
| 1F.4N | 0 |
| 2F.2N | 5 |
| 2F.4N | 1 |

The vials were capped under nitrogen, sterilized by gamma radiation, and stored. There were small losses of stannous ion during this procedure, referred to in the table of collected results.

EXAMPLE 2

Preparation of injection solution for bone scintigraphy

Vials from Example 1 were reconstituted by the addition of each of 8 ml of eluent saline from a technetium generator having a technetium activity of 200 mCi. The eluent had been stored under compressed air, and therefore contained a high concentration of dissolved oxygen. The loss of stannous ion relative to the amount present after completion of freeze-drying during reconstitution was determined:

| Formulation Code | % Loss of $Sn^{++}$ on Reconstitution |
| --- | --- |
| 1F | 45 |

-continued

| Formulation Code | % Loss of Sn$^{++}$ on Reconstitution |
| --- | --- |
| 2F | 45-50 |
| 1F.N5 | 6 |
| 1F.1N | 2 |
| 1F.2N | 8 |
| 1F.4N | 2 |
| 2F.N5 | 15 |
| 2F.1N | 7 |
| 2F.2N | 4 |
| 2F.4N | 0 |

EXAMPLE 3

Storage of injection solution for bone scintigraphy

The injection solutions prepared in Example 2 were stored for six hours. Then the concentration of stannous tin and pertechnetate were measured, with the following results:

| Formulation Code | Sn$^{2+}$ at 6 hours μ/ml | TcO$_4^-$ at 6 hours % |
| --- | --- | --- |
| 1F | <3 | ~25 |
| 2F | <3 to 3 | 7 to 8* |
| 2.5F | 3 to 6 | <0.2 |
| 1F.N5 | <3 | 1.9 |
| 1F.1N | 6 | 0.1 |
| 1F.2N | 9 | 0.1 |
| 1F.4N | 15 | 0 |
| 2F.N5 | 9 | 0 |
| 2F.1N | 9 | 0 |
| 2F.2N | 33 | 0 |
| 2F.4N | 30 | 0 |

*2F showed borderline stability at 6 hours. In five separate experiments the amount of TcO$_4^-$ varied widely, from 0.2% to 20%, averaging 7 to 8%, whereas 2.5F in many experiments consistently gave TcO$_4^-$ below 0.2%.

Pertechnetate was measured by thin layer chromatography on hydroxylapatite, and is expressed as a percentage of total technetium. Stannous ion content was measured by a starch iodine titration method, whose limit of sensitivity was 3 μg/ml. In formulations 1F and 1F.N5, the stannous ion content after 6 hours was less than 3 μg/ml (i.e. was possibly zero) and the pertechnetate content was appreciable. In formulation 2F, stannous ion was sometimes still just detectable and the pertechnetate content was just starting to rise. In all other formulations including 2.5F stannous ion was still present and no signficant amount of pertechnetate had been formed.

Collected results from experiments of the type described in Examples 1, 2 and 3

In the table below, the stannous tin remaining is expressed as a percentage of the stannous tin originally present in a dispensed aliquot of the bulk aqueous solution. The figures are averaged over many experiments. It is to be noted that the amount of stannous tin, remaining after reconstitution of the freeze-dried vials with 8 ml of TcO$_4^-$ eluant containing 200 mCi of Tc99m, is the same whether the vials are gamma sterilised or not. In either case, nitrate has a marked beneficial effect. The act of gamma sterilization appears to cause some loss of stannous tin when nitrate is present, but there then appears to be no further loss on reconstitution. On vials which have not been gamma sterilised, there appears to be a small loss on reconstitution even when nitrate is present.

|  | Gamma Sterilised | | not Gamma Sterilized | |
| --- | --- | --- | --- | --- |
|  | no nitrate | 2 to 4 mg nitrate | no nitrate | 2 to 4 mg nitrate |
| After dispensing and freeze-drying | 80 | 95-100 | 80 | 95-100 |
| After gamma sterilisation | 75-80 | 90 | 80 | 95-100 |
| After reconstitution | 45 | 90 | 45 | 90 |

EXAMPLE 4

Preparation of gluconate injection solution for kidney scanning

A gluconate agent for kidney scanning was prepared by dispensing aqueous solutions of calcium gluconate and stannous chloride under nitrogen into vials so that each contained:

150 mg: calcium gluconate
0.3 mg: SnCl$_2$.2H$_2$O

The solutions were freeze-dried, and the vials capped under nitrogen and sterilised by gamma radiation. The tin content of each vial was 157.8 μg; the stannous ion content of each vial was determined to be 134 μg before irradiation and 111 μg after irradiation.

To each of six vials was added 6 mls of the eluate of a one-day old technetium generator, the eluate containing about 175 mCi of activity. To three of the vials was also added 50 μl of 2% sodium nitrate solution. The vials were stored and samples were analysed for pertechnetate (as a percent of total technetium) at intervals, with the following results:

| Vial Number | NaNO$_3$ concentration | % Pertechnetate | | |
| --- | --- | --- | --- | --- |
|  |  | 0.5 hr | 3.5 hr | 6.0 hr |
| 1 | — | <0.2 | 5.5 | 14.5 |
| 2 | 1 mg | <0.2 | 1.0 | 3.6 |
| 3 | — | <0.2 | 1.4 | 5.8 |
| 4 | 1 mg | <0.2 | 0.9 | 3.5 |
| 5 | — | <0.2 | 4.9 | 14.1 |
| 6 | 1 mg | <0.2 | 0.7 | 3.3 |

EXAMPLE 5

A piece of tin foil 5×10 mm in area and 0.1 mm thick, of 99.5% purity, was degreased and then activated for one minute in concentrated hydrochloric acid followed by washing in ethanol. To a vessel containing this piece of tin foil, 5 mg of methylene diphosphonic acid and sodium bicarbonate buffer, was added 1 ml of eluant saline from a technetium generator containing 20 mCi of Tc-99m. The liquid mixture was left for 15 minutes. Labelling efficiency was 98.5%.

The experiment was repeated but using 8 ml of eluant saline containing 200 mCi of Tc-99m. After 15 minutes the labelling yield was less than 90% and on leaving the mixture in the presence of the tin, the amount of pertechnetate increased over a period of time, so that the amount of MDP complex after 5 hours was only 60%.

This last experiment was repeated but in the presence of 4 mg of sodium nitrate. A quantitive yield of the MDP complex was obtained in 15 minutes.

EXAMPLE 6

Two experiments designated (a) and (b) were carried out side by side. In each was employed tin metal, MDP, and sodium bicarbonate buffer, as in the last example, together with 8 ml of eluant saline containing 200 mCi of Tc-99m.

(a) At 1 hour, 10% of $TcO_4^-$ was present, and the amount increased with further storage.

(b) At 1 hour, 10% of $TcO_4^-$ was present. 4 mg of sodium nitrate was then added. The amount of $TcO_4^-$ was rapidly reduced to zero, and remained zero for some hours.

EXAMPLE 7

The effect of sodium nitrate as a stabiliser was examined in $^{99m}Tc$-MDP preparations containing up to 295 mCi of $^{99m}Tc$ activity at the time of reconstitution.

The vial contents of 5.0 mg methylenediphosphonic acid (as sodium salt) and 0.34 mg stannous fluoride under nitrogen gas, were reconstituted with 8 ml eluate from a $^{99m}Tc$ generator, the pressure within the vial being equalised by removal of the same volume of gas from the vial. Immediately after reconstitution the tabulated weight of sodium nitrite in 0.01–1.0 ml physiological saline solution was injected into the vial. After mixing by vial inversion, 10.0 ml air were drawn through the gas phase above the liquid vial contents using a syringe and bleed needle. A small sample, less than 0.1 ml was then withdrawn for radiochemical analysis by thin-layer chromatography on hydroxylapatite with physiological saline eluent. Further samples for identical analysis were removed at 3 hours and again at 6 hours after the time of reconstitution.

The slides were cut in half and the solvent front and origin halves counted separately in a sodium iodide well counter. The $TcO_4^-$ present was expressed as % of total technetium as follows:

$$\frac{\text{Counts at solvent front-background}}{(\text{Counts at solvent front} + \text{counts at origin}) - (2 \times \text{background counts})} \times 100\%$$

The stannous content was measured, 6 hours after reconstitution by titration with an iodine solution of known strength, using starch as indicator.

The results obtained at 6 hours are tabulated below:

| $^{99m}Tc$ Activity at reconstitution (mCi) | Wt of $NaNO_2$ added per vial | % $TcO_4^-$ | $\mu g$ $Sn^{2+}$/ml |
|---|---|---|---|
| | | 6 hours after reconstitution | |
| 214 | 1.0 mg | <0.1% | * |
| 109 | 0.1 mg | <0.1% | 15 |
| 295 | 0.1 mg | <0.1% | 21 |
| 221 | 0.01 mg | 11.9% | <3 |

*Biodistribution measured on this preparation.

Mean biodistribution results:

| | |
|---|---|
| Bone | 50.22% of injection dose |
| Stomach + Gut | 1.74% of injection dose |
| Bone:Muscle | 471 |
| Bone:Blood | 204 |
| Bone:Liver + Spleen | 253 |

We claim:

1. In a method of making a radiopharmaceutical composition by mixing an aqueous solution of pertechnetate with a reducing agent comprising tin as metal or $Sn^{++}$ to reduce the pertechnetate and a complexing agent to form a complex with the reduced technetium, the improvement which comprises incorporating in the composition a nitrate or nitrite or a mixture of said nitrate and nitrite in an amount to diminish oxidation of $Sn^{2+}$ to $Sn^{4+}$ during preparation and storage of the complex.

2. The method as claimed in claim 1, wherein there is provided a first-formed mixture of the reducing agent comprising tin, the complexing agent and the nitrate, nitrite or mixture of said nitrate and nitrite, and the aqueous solution of pertechnetate is subsequently added to this first-formed mixture.

3. The method as claimed in claim 2, wherein the first-formed mixture is formed by dispensing and freeze-drying solutions of stannous ion, the complexing agent and the nitrate, nitrite or mixture of said nitrate and nitrite.

4. The method as claimed in claim 2, wherein the first-formed mixture is formed by providing a piece of metallic tin and dispensing and freeze-drying solutions of the complexing agent and the nitrate, nitrite or mixture of said nitrate and nitrite.

5. The method as claimed in claim 2, wherein the first-formed mixture is made sterile.

6. The method as claimed in claim 1, wherein, the solution of pertechnetate has an activity of up to about 500 mCi, there is used from 0.01 mg to 5.0 mg of nitrite, expressed as sodium nitrate, or from 0.1 mg to 50 mg of nitrate, expressed as sodium nitrate, or a mixture of said nitrite and nitrate.

7. A reagent which forms, on addition of an aqueous solution of pertechnetate, a radiopharmaceutical composition, which reagent comprises in a sterile state a stannous tin reducing agent for the pertechnetate, a complexing agent to form a complex with the reduced technetium, and nitrate or nitrite ion or a mixture of nitrate and nitrite ions in an amount to diminish oxidation of $Sn^{2+}$ to $Sn^{4+}$ during preparation and storage of the reagent and of the complex.

8. A reagent which forms, on addition of an aqueous solution of pertechnetate, a radiopharmaceutical composition, which reagent comprises in a sterile state a tin metal reducing agent for the pertechnetate, a complexing agent to form a complex with the reduced technetium, and nitrate or nitrite ion or a mixture of nitrate and nitrite ions in an amount to diminish oxidation of $Sn^{2+}$ to $Sn^{4+}$ during preparation and storage of the complex.

9. The reagent as claimed in claim 7 or claim 8, wherein there is present from 0.01 mg to 5.0 mg of nitrite, expressed as sodium nitrite, or from 0.1 mg to 50 mg of nitrate, expressed as sodium nitrate or a mixture of said nitrate and nitrite.

* * * * *